(12) United States Patent
Jaeger et al.

(10) Patent No.: US 10,352,943 B2
(45) Date of Patent: Jul. 16, 2019

(54) A-FUCOSYLATION DETECTION IN ANTIBODIES

(71) Applicant: Roche Glycart AG, Schlieren (CH)

(72) Inventors: Christiane Jaeger, Wallisellen (CH); Hans Koll, Schwabhausen (DE); Peter Sondermann, Stockdorf (DE); Pablo Umana, Wollerau (CH)

(73) Assignee: Roche Glycart AG (CH)

( * ) Notice: Subject to any disclaimer, the term of this patent is extended or adjusted under 35 U.S.C. 154(b) by 87 days.

(21) Appl. No.: 15/179,431

(22) Filed: Jun. 10, 2016

(65) Prior Publication Data
US 2017/0108510 A1   Apr. 20, 2017

Related U.S. Application Data

(63) Continuation of application No. 14/285,440, filed on May 22, 2014, now abandoned, which is a continuation of application No. 13/499,887, filed as application No. PCT/EP2010/064291 on Sep. 28, 2010, now abandoned.

(30) Foreign Application Priority Data

Oct. 2, 2009   (EP) .................................... 09172130

(51) Int. Cl.
| | | |
|---|---|---|
| G01N 33/68 | (2006.01) | |
| G01N 33/53 | (2006.01) | |
| C12Q 1/37 | (2006.01) | |
| C07K 16/00 | (2006.01) | |
| C12Q 1/40 | (2006.01) | |

(52) U.S. Cl.
CPC ......... *G01N 33/6854* (2013.01); *C07K 16/00* (2013.01); *C12Q 1/37* (2013.01); *C12Q 1/40* (2013.01); *C12Y 302/01* (2013.01); *C12Y 302/01096* (2013.01); *C12Y 304/17002* (2013.01); *C12Y 304/21007* (2013.01); *G01N 33/5308* (2013.01); *C07K 2317/41* (2013.01); *C07K 2317/52* (2013.01); *G01N 2333/924* (2013.01); *G01N 2333/948* (2013.01); *G01N 2333/968* (2013.01); *G01N 2400/02* (2013.01); *G01N 2440/38* (2013.01); *G01N 2560/00* (2013.01)

(58) Field of Classification Search
None
See application file for complete search history.

(56) References Cited

U.S. PATENT DOCUMENTS

| | | |
|---|---|---|
| 5,126,250 A | 6/1992 | McDonough et al. |
| 2007/0166306 A1 | 7/2007 | Fey et al. |

FOREIGN PATENT DOCUMENTS

| | | |
|---|---|---|
| JP | 2005-069846 | 3/2005 |
| WO | 2008/077546 A1 | 7/2008 |
| WO | 2008/128228 A1 | 10/2008 |
| WO | 2009/033670 A2 | 3/2009 |
| WO | 2009/033670 A3 | 3/2009 |
| WO | 2009/033670 A8 | 3/2009 |

OTHER PUBLICATIONS

Allhorn et al., "Human IgG/Fc gamma R Interactions Are Modulated by Streptococcal IgG Glycan Hydrolysis" PLoS ONE 3(1):1-12 ( 2008).
Antes et al., "Analysis of lysine clipping of a humanized Lewis-Y specific IgG antibody and its relation to Fc-mediated effector function" Journal of Chromatography B 852:250-256 (2007).
Collin et al., "EndoS, a novel secreted protein from *Streptococcus pyogenes* with endoglycosidase activity on human IgG" The EMBO Journal 20(12):3046-3055 ( 2001).
Elbers et al., "Influence of Growth Conditions and Developmental Stage on N-Glycan Heterogeneity of Transgenic Immunoglobulin G and Endogenous Proteins in Tobacco Leaves" Plant Physiology 126:1314-1322 ( 2001).
Ferrara et al., "Modulation of therapeutic antibody effector functions by glycosylation engineering: influence of Golgi enzyme localization domain and co-expression of heterologous beta1, 4-N-acetylglucosannnyluansferase III and Golgi alpha-mannosidase II" Biotechnology and Bioengineering 93(5):851-861 ( 2006).
Harvey, "Matrix-assisted laser desorption/ionization mass spectrometry of carbohydrates and glycoconjugates" Int J Mass Spectrom 226:1-35 ( 2003).
Huhn et al., "IgG glycosylation analysis" Proteomics 9:882-913 ( 2009).
Mimura et al., "Contrasting glyco sylation profiles between Fab and Fc of a human IgG protein studied by electrospray ionization mass spectrometry" Journal of Immunological Methods 326: 116-126 (2007).
Papac et al., "A high-throughput microscale method to release N-linked oligosaccharides from glycoproteins for matrix-assisted laser desorption/Ionization time-of-flight mass spectrometric analysis" Glycobiology 8(5):445-454 ( 1998).
Schuster et al., "Improved effector functions of a therapeutic monoclonal Lewis Y-specific antibody by glycoform engineering" Cancer Res 65(17):7934-7941 (Sep. 1, 2005).
Tarentino et al., "Deglycosylatjon of Asparagine-Linked Glycans by Peptide:N-Glycosidase F" Biochemistry-US 24(17):4665-4671 ( 1985).
Umana et al., "Engineered glycoforms of an antineuroblastoma IgG1 with optimized antibody-dependent cellular cytotoxic activity" Nat Biotechnol 17:176-180 (Feb. 1999).
Zhou et al., "Development of A Simple and Rapid Method for Producing Non-Fucosylated Oligomannose Containing Antibodies With Increased Effector Function" Biotechnology and Bioengineering 99(3):652-655 (Feb. 2008).

(Continued)

*Primary Examiner* — Paul J Holland

(74) *Attorney, Agent, or Firm* — Frank Berendt

(57) ABSTRACT

This invention describes a new analytical method to determine the quantity and distribution of fucose per Fc within an antibody preparation.

10 Claims, 18 Drawing Sheets

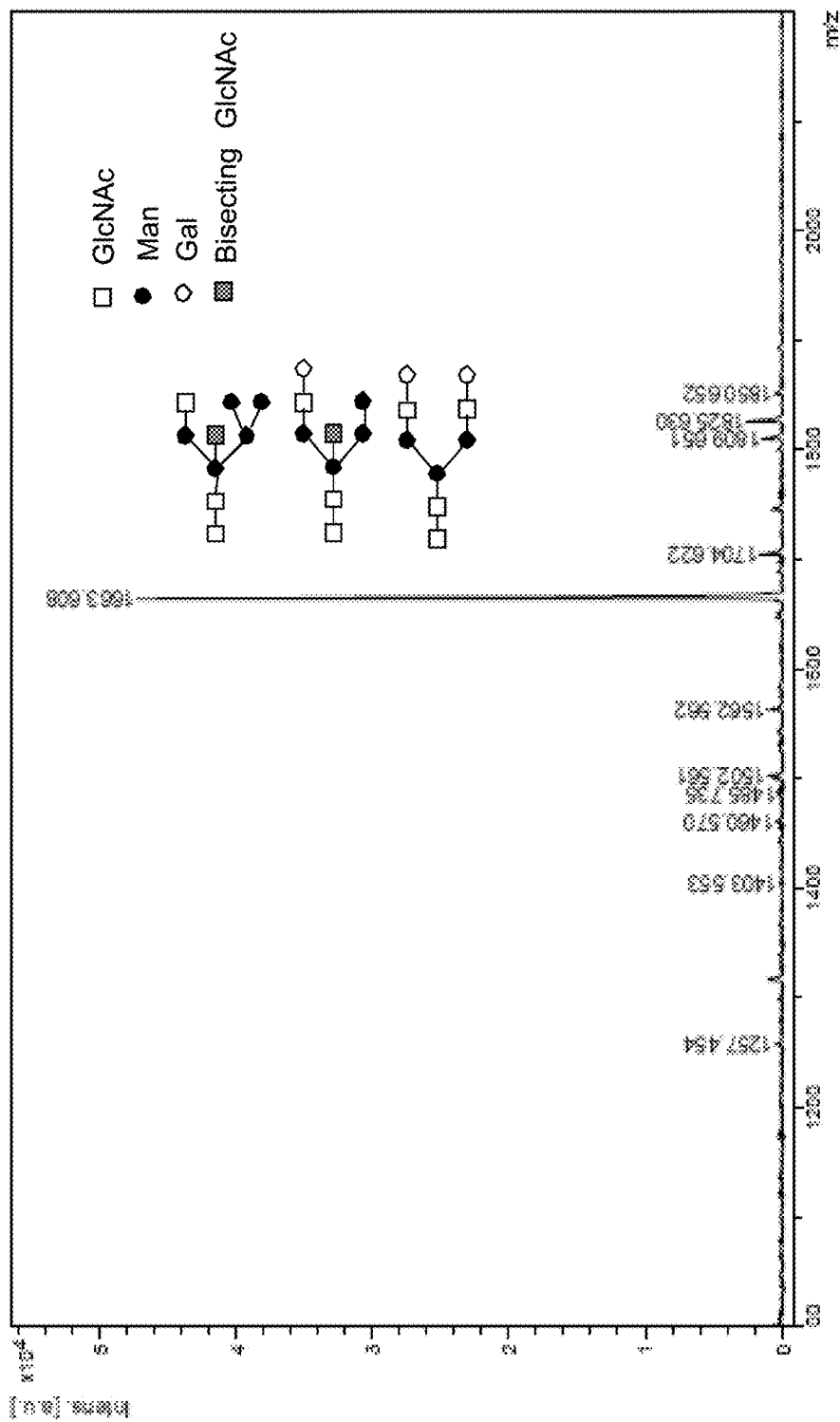

A-FUCOSYLATION DETECTION IN ANTIBODIES

RELATED APPLICATIONS

This application is a continuation of U.S. patent application Ser. No. 14/285,440, filed May 22, 2014 (now abandoned), which is a continuation of U.S. patent application Ser. No. 13/499,887 filed Apr. 2, 2012 (now abandoned), which is a 35 U.S.C. § 371 based on International Application PCT/EP2010/064291 having an international filing date of Sep. 28, 2010, the entire contents of which are incorporated herein by reference, and which claims benefit under 35 U.S.C. § 119 to European Patent Application No. 09172130.8 filed Oct. 2, 2009.

This invention relates to a method for detecting the presence or absence of fucose residues within a glycosylated antibody or a fragment thereof.

BACKGROUND

Figure 1:
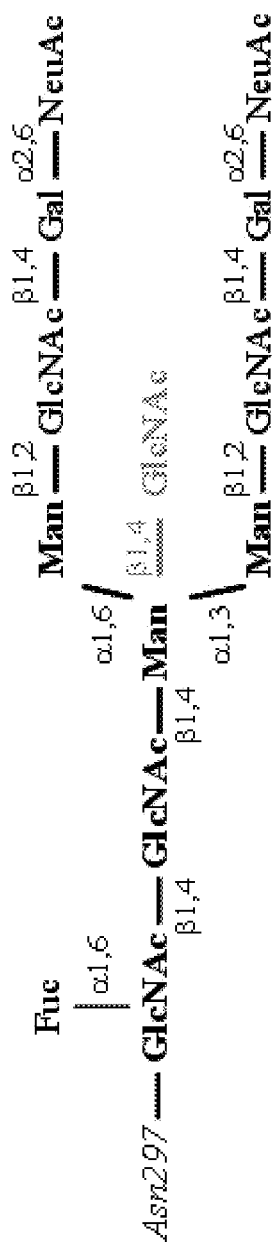

While the variable regions within the Fab (fragment antigen binding) domains of antibodies are responsible for the recognition of the antigen, the Fc (fragment crystallizable) region represents an invariant part of the antibody that is responsible for the mediation of effector functions. In the case of immunoglobulin G (IgG) these encompass the fixation of complement and the binding to Fcγ receptors (FcγRs). The presence of an N-linked oligosaccharide at a single conserved site (Asn297) within the CH2 domain of the homodimeric Fc fragment is mandatory for the mediation of both of these effector functions. It was only recently discovered that modification of the attached carbohydrates can also have an affinity improving effect for the interaction between FcγRIIIa and IgG. The carbohydrate modification responsible for this effect is the absence of a fucose residue which is usually attached to the first N-acetylglucosamine (GlcNAc) residue in the biantennary complex-type IgG glycan (FIG. 1).

It could be demonstrated by in vivo and in vitro experiments that such increased affinity results in enhanced antibody-dependent cellular cytotoxicity (ADCC) mainly mediated by natural killer (NK) cells. Consequently, it is also believed that such a-fucosylated antibodies have an improved efficacy in treatments that aim to eradicate opsonized cells.

The generation of a-fucosylated antibodies represents an important biotechnological challenge which can be achieved by several methods. While cell lines with a complete depletion of enzymes involved in the biosynthesis of fucosylation (e.g. by gene knockout) may yield quantitatively a-fucosylated antibodies, most other methods do not. For example, siRNA treatment or co-cultivation of antibody-expressing cells with kifunensine (Zhou et al., Biotechnol Bioeng (2008) 99, 652-665), as well as carbohydrate modification by N-acetylglucosaminyltransferase III (GnT-III), which promotes the formation of bisected oligosaccharides consequently inhibiting the fucosylation reaction (Umana et al., Nat Biotech (1999) 17, 176-180), lead to only partially a-fucosylated antibodies.

These partially a-fucosylated antibodies can principally exhibit a heterogeneous a-fucosylation distribution within a pool of antibodies. For example, fucosylation rates can be different during fermentation. Also, the event of fucosylation could be cooperative, i.e. the second fucosylation on the homodimeric antibody may occur with an increased (positive cooperativity) or decreased (negative cooperativity) rate compared to the first one.

The FcγRIIIa/IgG complex has a 1:1 stoichiometry but IgG has two binding sites for FcγRIIIa. Consequently, in a single a-fucosylated antibody the receptor can bind with high affinity to the binding site formed by the IgG's a-fucosylated glycan and protein core or with low affinity to the binding site consisting of the fucosylated carbohydrate and the protein core. It can therefore be concluded that a pool of antibodies with 50% a-fucosylation may consist of a homogeneous population of antibodies in which only one of the two N-glycans is fucosylated, or 50% of antibodies in which both N-glycans are fucosylated while in the other 50% none of the N-glycans are fucosylated. It is obvious that such a differential partition of a-fucosylation influences the overall affinity to FcγRIIIa and results in a different biological activity. It is therefore mandatory to analyze the biological activity of such an antibody preparation either directly by employing a biological test system (bioassay) or indirectly by biochemically measuring the rate and distribution of the a-fucosylation, which yields a more exact result.

The current state-of-the-art glycoanalytics uses N-glycosidase F (PNGase F) from *Flavobacterium meningosepticum* to cleave off the N-linked carbohydrates with a subsequent MALDI-MS (matrix-assisted laser desorption ionization mass spectrometry) analysis (according to Papac et al., Glycobiology (1998) 8, 445-454). By employing such a process, however, the linkage information is lost and the determination of fucosylation distribution within an antibody preparation is not possible.

On the other hand, analysis of the complete antibody using ESI-MS (electrospray ionization mass spectrometry) yields complex mass patterns that do not allow a quantitative interpretation due to the various modifications other than fucosylation—like galactosylation, C-terminal lysine heterogeneity, deamidation etc.—that may or may not occur in both subunits of the homodimeric IgG.

Therefore, there is a need for a new analytical method that eliminates the mentioned heterogeneity but maintains the linkage information.

DESCRIPTION OF THE INVENTION

The above described drawbacks are overcome by this invention, which provides for methods for detecting the presence or absence of fucose residues within a glycosylated antibody. Preferably, the quantity of fucose residues and their distribution pattern within an antibody or a fragment thereof are determined. The analysis of the distribution of fucose residues per Fc molecule in an antibody preparation is also part of this invention. In addition, the present invention can be used for the determination of cooperative fucosylation in an antibody preparation during fermentation. Hence, this invention provides for a method that closes a gap in antibody analytics. With the knowledge of fucosylation patterns within an antibody or fragment thereof gained by means of this new method, a more accurate prediction of Fc-mediated potency is now possible.

Surprisingly, the inventors of the present invention found that Endo S (an enzyme with endoglycosidase activity, originally identified in *Streptococcus pyogenes* (Collin and Olsen, EMBO J (2001) 20, 3046-3055)) cleaves the complex-type glycan moieties from the Fc region of human IgG, leaving behind just the first GlcNAc residue to which a fucose residue might be attached. The hybrid-type carbohydrates that are discriminated (spared) by Endo S can be quantitatively cleaved at the same site by Endoglycosidase H (Endo H). The combination of both enzymes thus allows the preparation of a uniformly glycosylated protein that only varies by the fucose content. Analysis of such treated Fc fragments not only allows the determination of the fucose content of, but also determination of the distribution of fucose residues within the analyzed antibody pool. These new findings close an analytical gap and may allow a potency estimation of the analyzed antibody in terms of its efficacy in ADCC induction.

Accordingly, the present invention relates to a method for detecting the presence or absence of fucose residues within a glycosylated antibody or a fragment thereof.

In one embodiment the inventive method comprises the following steps:
a) removal of all heterogeneous saccharide residues from the protein,
b) removal of all other heterogeneous residues from the protein,
c) subsequent analysis of the protein.

In another embodiment, step c) of said method additionally comprises a purification step prior to analysis. In a specific embodiment purification is achieved by affinity chromatography or size exclusion chromatography. Affinity chromatography can be performed using for example Protein A or Protein G.

In one embodiment the protein to be treated and analyzed by the method of the invention is an antibody or an antibody fragment. Preferably said antibody is an IgG type antibody. Said antibody fragment is preferably an Fc fragment, in particular an Fc fragment of an IgG type antibody.

In a specific embodiment the removal of step a) is performed by one or more enzymes that specifically cleave complex-type or hybrid-type N-linked carbohydrates. Preferably, these enzymes comprise Endo S and Endo H.

In another specific embodiment the removal of step b) is performed by one or more enzymes. Preferably these enzymes comprise plasmin and/or carboxypeptidase B.

In a further specific embodiment the analysis of step c) comprises CE-SDS MW (capillary electrophoresis-sodium dodecyl sulfate molecular weight) analysis, ESI-MS analysis or liquid chromatography-mass spectrometry (LC-MS), or a combination thereof.

In a preferred embodiment, step a) of the above described method comprises cleavage of the heterogeneous saccharides from the carbohydrate structures of the protein after the first GlcNAc residue of said structures, thereby leaving the fucose residue attached to the antibody core. This step can be performed with two enzymes that specifically cleave complex-type or hybrid-type N-linked carbohydrates that frequently occur in biotechnologically produced antibodies, for example Endo S and Endo H.

In a preferred embodiment, step b) of the above described method comprises quantitative removal of C-terminal lysine residues of the antibody heavy chain, preferably using an enzyme, said enzyme preferably comprising carboxypeptidase B.

In another preferred embodiment, step b) of the above described method comprises cleavage between the Fab and the Fc fragment of an antibody. Preferably the covalent interchain disulphide bridges within the hinge peptide of the heavy chains are maintained within the Fc-fragment after cleavage between the Fab and the Fc fragment. Preferably the cleavage is achieved by an enzyme. Preferably such enzyme comprises plasmin.

In a preferred embodiment, step c) of the above described method comprises analysis of the treated antibody molecule or Fc fragment by LC-MS without any prior purification steps. Such an analysis normally yields only three masses that correspond to proteins with two fucosylated glycans, proteins with one fucosylated and one a-fucosylated glycan, and proteins in which both glycans are a-fucosylated.

In another embodiment, step c) of the above described method comprises purifying the treated antibody molecule or Fc fragment using standard methods and analyzing it by ESI-MS analysis. Such an analysis normally yields only three masses that correspond to proteins with two fucosylated glycans, proteins with one fucosylated and one a-fucosylated glycan, and proteins in which both glycans are a-fucosylated.

In one embodiment the method of the invention comprises the following steps: providing an antibody preparation, optionally isolating the Fc fragment portion of such antibody preparation, removing all heterogeneous saccharide residues from said antibody or Fc fragment with Endo H and Endo S, removing C-terminal lysine residues from said antibody or Fc fragment with carboxypeptidase B, and analysis of the treated antibody or Fc fragment by ESI-MS, LC-MS or CE-SDS MW analysis.

In another embodiment said method comprises the following steps: providing an antibody preparation, optionally isolating the Fc fragment portion of such antibody preparation using plasmin, removing all heterogeneous saccharide residues from said antibody or Fc fragment with Endo H and Endo S, removing C-terminal lysine residues from said antibody or Fc fragment with carboxypeptidase B, and purification and analysis of the treated antibody or Fc fragment by ESI-MS, LC-MS or CE-SDS MW analysis.

In yet another embodiment, this invention is directed to kits suitable for performing an assay which detects the presence or absence of fucose residues within a glycoprotein. The kits of this invention comprise all components referred to in the methods described above (e.g. Endo H, Endo S, carboxypeptidase B, plasmin, suitable buffers), instructions setting forth a procedure according to any one of the methods described above and a container for the contents of the kit.

Use of Endo S for cleavage of complex-type N-linked oligosaccharides of a glycoprotein, preferably a glycosylated antibody or a fragment thereof, is also part of this invention.

Definitions

Terms are used herein as generally used in the art, unless otherwise defined in the following:

The term "heterogeneous saccharide" as used herein, includes any monosaccharide moiety of a glycosylated antibody or antibody fragment that is not connected to a fucose residue. Non-limiting examples for heterogeneous saccharides of a glycosylated antibody or antibody fragment are mannose, sialate, galactose, acetylglucosamine. Generally, heterogeneous saccharides which are removed in step a) of the method according to the invention will be all saccharides other than the first GlcNAc residue, i.e. the GlcNAc residue attached to an asparagine residue of the protein, and the fucose residue linked to that first GlcNAc residue.

The term "heterogeneous residues" as used herein, means any other moiety of a glycosylated antibody or antibody fragment (other than heterogenous saccharides) that could interfere with the detection of fucose residues within said antibody or antibody fragment. Non-limiting examples of heterogenous residues are various modifications of the glycosylated antibody or antibody fragment other than fucosylation, such as galactosylation, C-terminal lysine heterogeneity and deamidation. The term "heterogeneous residues" may further include antibody fragments that are not glycosylated, for example the Fab fragment, the scFv fragment and other fragments.

As used herein, the term "antibody" is intended to include whole antibody molecules, antibody fragments, or fusion proteins that include a region equivalent to the Fc region of an immunoglobulin.

Figure 7:
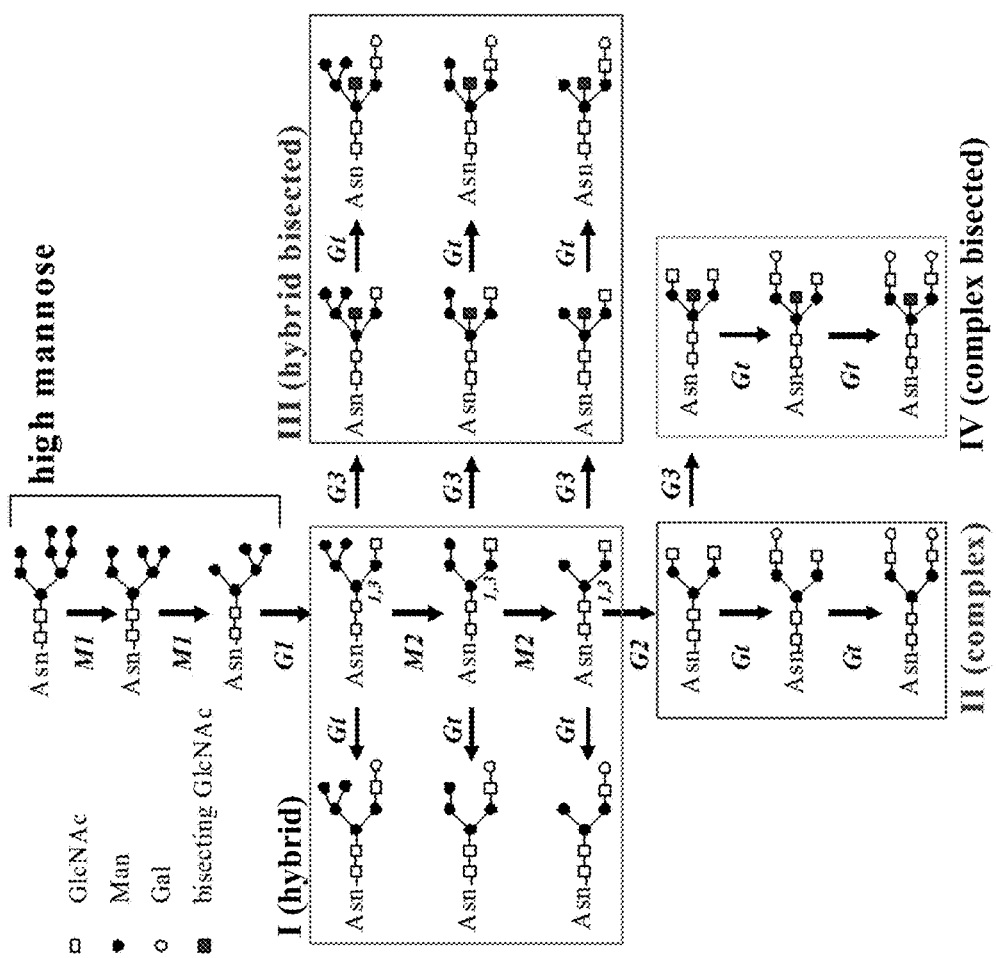

The terms "complex-type oligosaccharide" and "hybrid-type oligosaccharide" refer to the glycosylation pattern of an antibody or antibody fragment. Non-limiting examples of "complex-type oligosaccharide" and "hybrid-type oligosaccharide" are shown in FIG. 7. As understood by those skilled in the art, glycoproteins enriched in bisected hybrid-type oligosaccharides typically result from overexpression of GnT-III in production cell lines. Exemplary structures of bisected hybrid type oligosaccharides are detailed in FIG. 7-III, Glycoproteins enriched in bisected complex type oligosaccharides typically result from a co-expression of Mann and GnT-III in production cell lines. Exemplary structures of bisected, complex-type oligosaccharides are detailed in FIG. 7-IV (Ferrara et al., Biotechnol Bioeng (2006) 93, 851-861).

Cleavage "after" a sugar residue, as used herein, means cleavage distal to this residue, i.e. cleavage of the sugar bond linking this residue with the adjacent one towards the outer end of the carbohydrate structure. Cleavage "after the first GlcNAc residue" of an N-linked glycan means cleavage of the chitobiose core of the oligosaccharide, between the first (i.e. attached to the asparagine residue) and the second (i.e. attached to the first) GlcNAc residue.

"Distribution" of fucose residues within an antibody preparation refers to the presence within that preparation of antibody or Fc molecules differing in the number of fucose residues associated with the N-linked glycans in the Fc region. For example, an IgG molecule has two N-linked glycans in its Fc region, each of which can have a fucose residue linked to the first Gig residue of the carbohydrate structure. Thus, in an IgG preparation there might be three different molecular species: IgG with two, one or no fucose residues associated with the N-linked glycans in the Fc region. The ratio of these different species (i.e. the distribution of fucose residues per Fc molecule) can be determined by the method of the invention, in addition to determination of the total fucose content, i.e. the fraction of fucosylated or a-fucosylated N-glycans.

The examples below explain the invention in more detail. The examples are given to enable those skilled in the art to more clearly understand and practice the invention. The present invention, however, is not limited in scope by the exemplified embodiments, which are intended as illustrations of single aspects of the invention only, and methods which are functionally equivalent are within the scope of the invention.

SHORT DESCRIPTION OF THE FIGURES

FIG. 1. Schematic representation of a carbohydrate moiety attached to Asn-297 of human IgG1-Fc. The sugars in bold define the pentasaccharide core of N-linked glycan structures; the addition of the other sugar residues is variable. In grey is represented a bisecting GlcNAc residue.

Figure 2A:
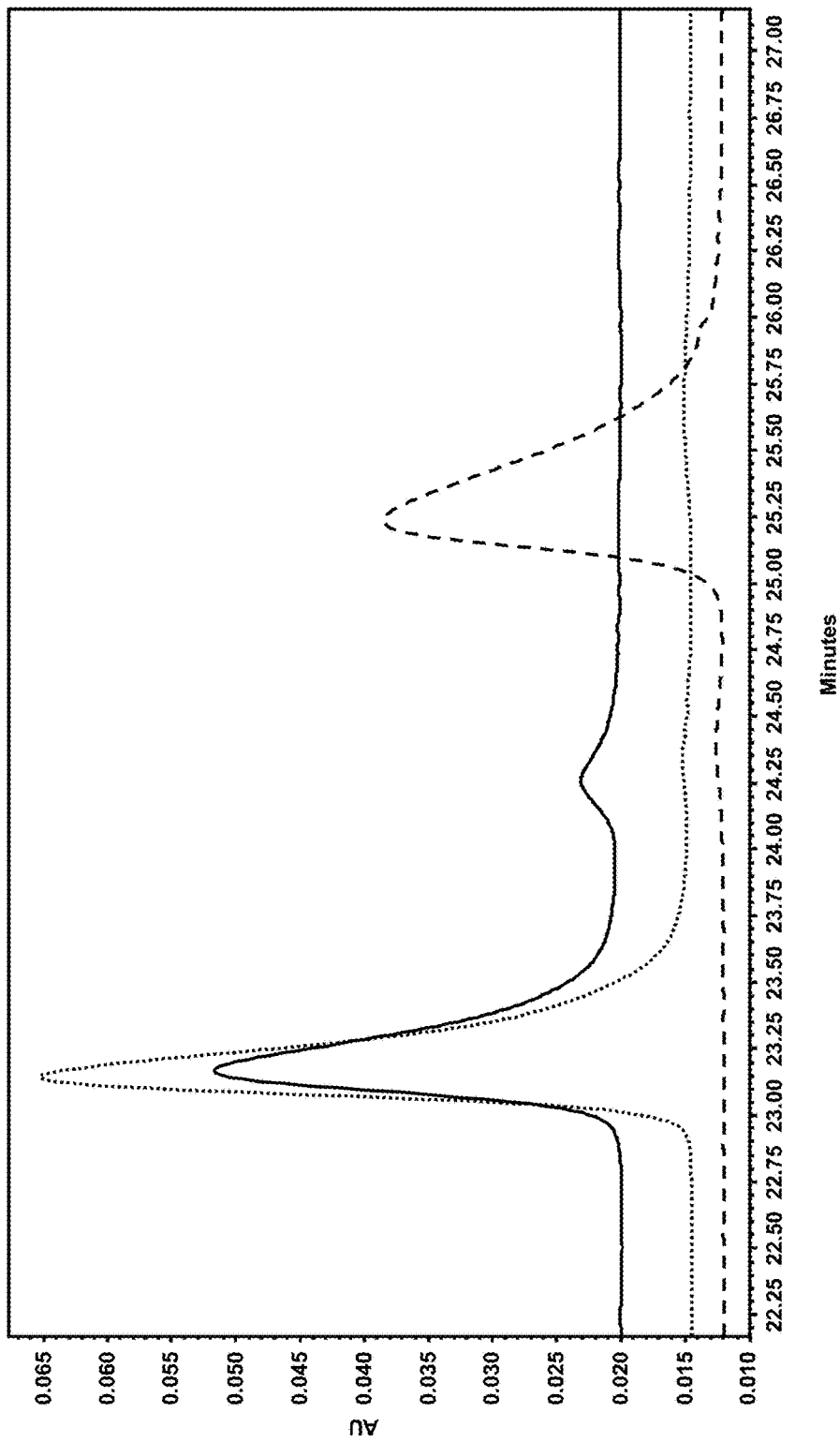
Figure 2B:
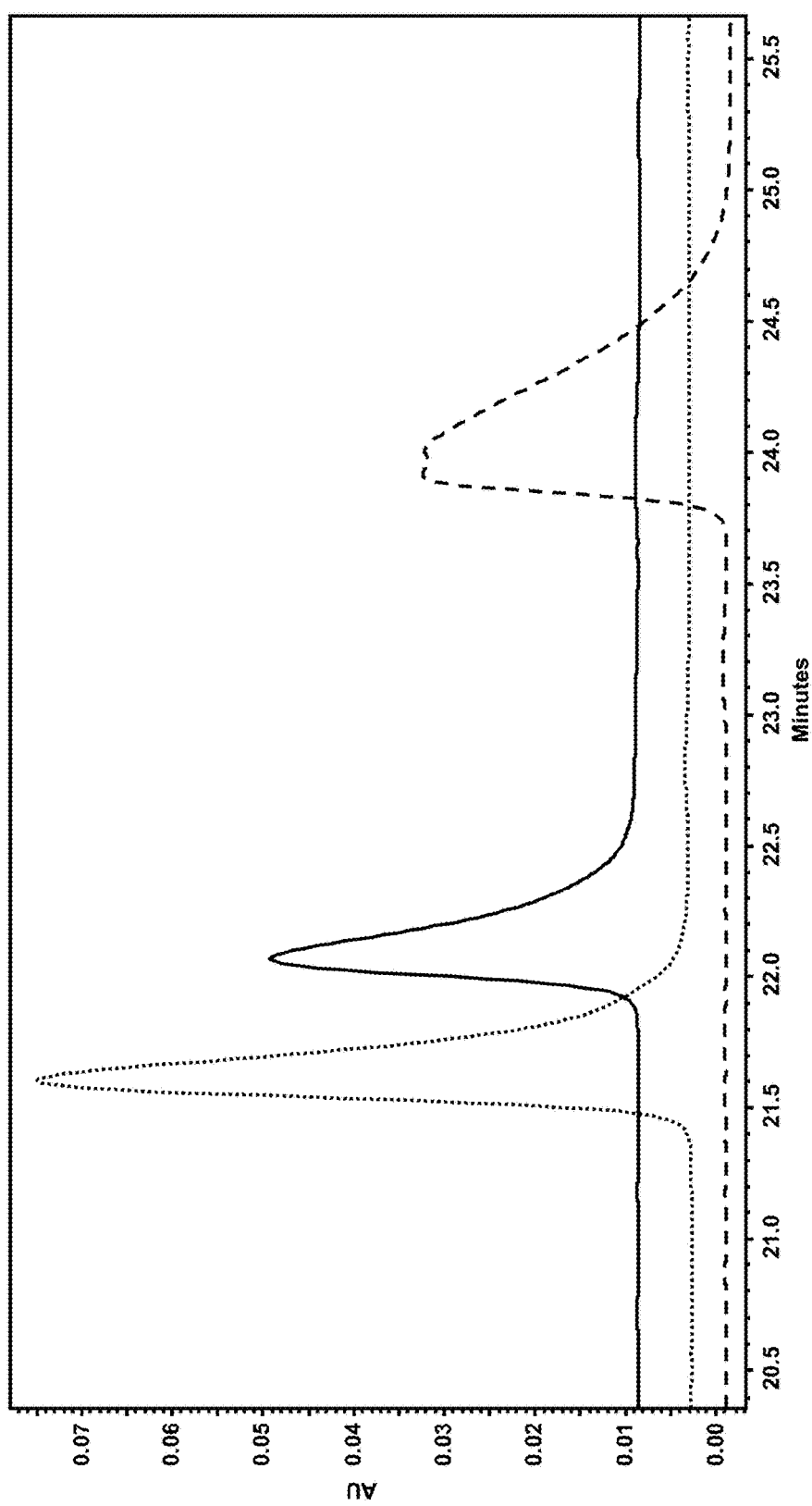

FIGS. 2A and 2B. Deglycosylation of intact Fc fragment of antibodies A (wildtype) and C (glycoengineered) monitored by CE-SDS. Electropherograms of non-reduced Fc fragments are shown before and after enzymatic treatment. (FIG. 2A) Fc fragment of antibody C without enzymatic treatment (dashed line) and deglycosylated with PNGase F (dotted line) or Endo S (solid line), (FIG. 2B) Fc fragment of antibody A without enzymatic treatment (dashed line), deglycosylated with PNGase F (dotted line) or deglycosylated with Endo S (solid line).

Figure 3A:
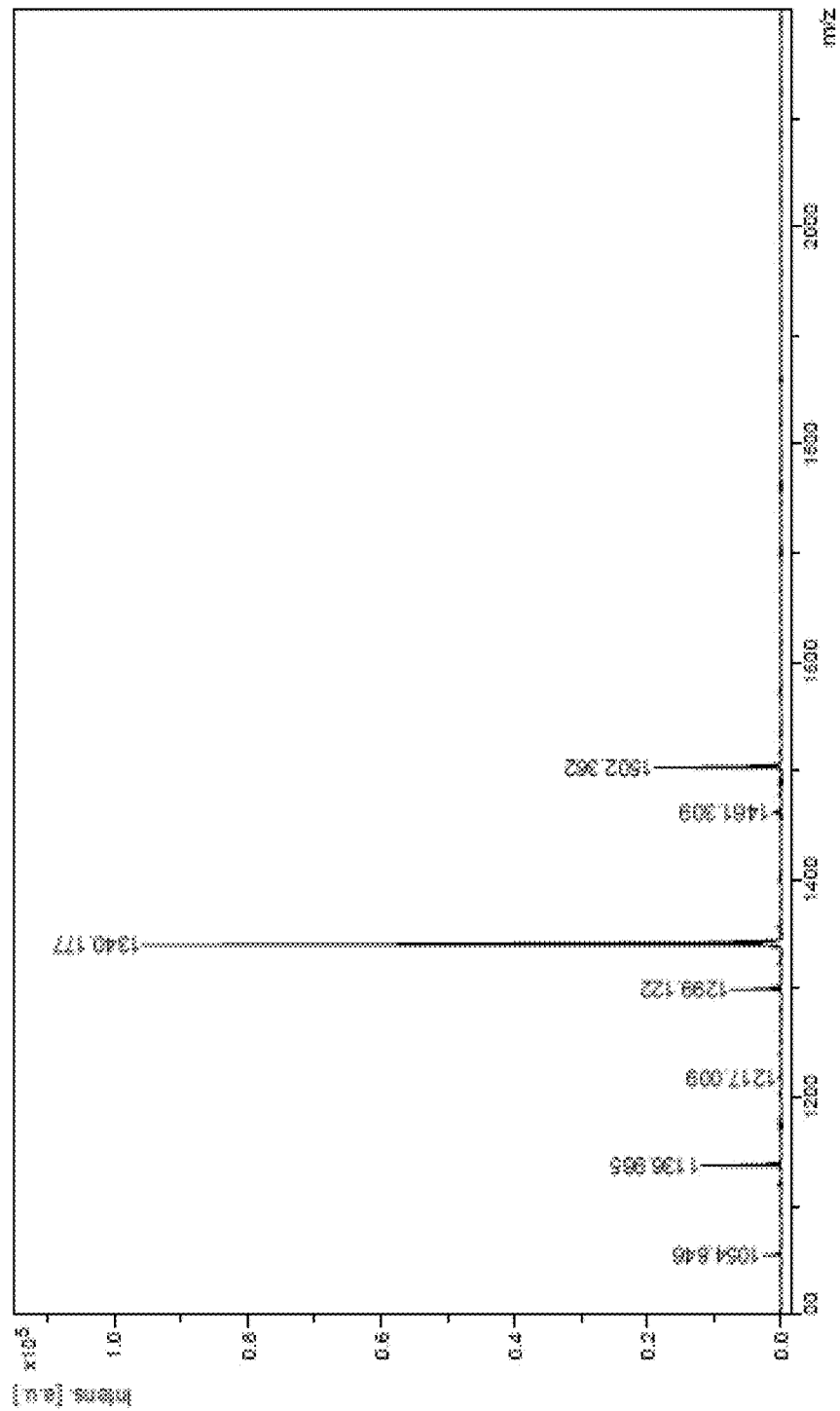
Figure 3C:
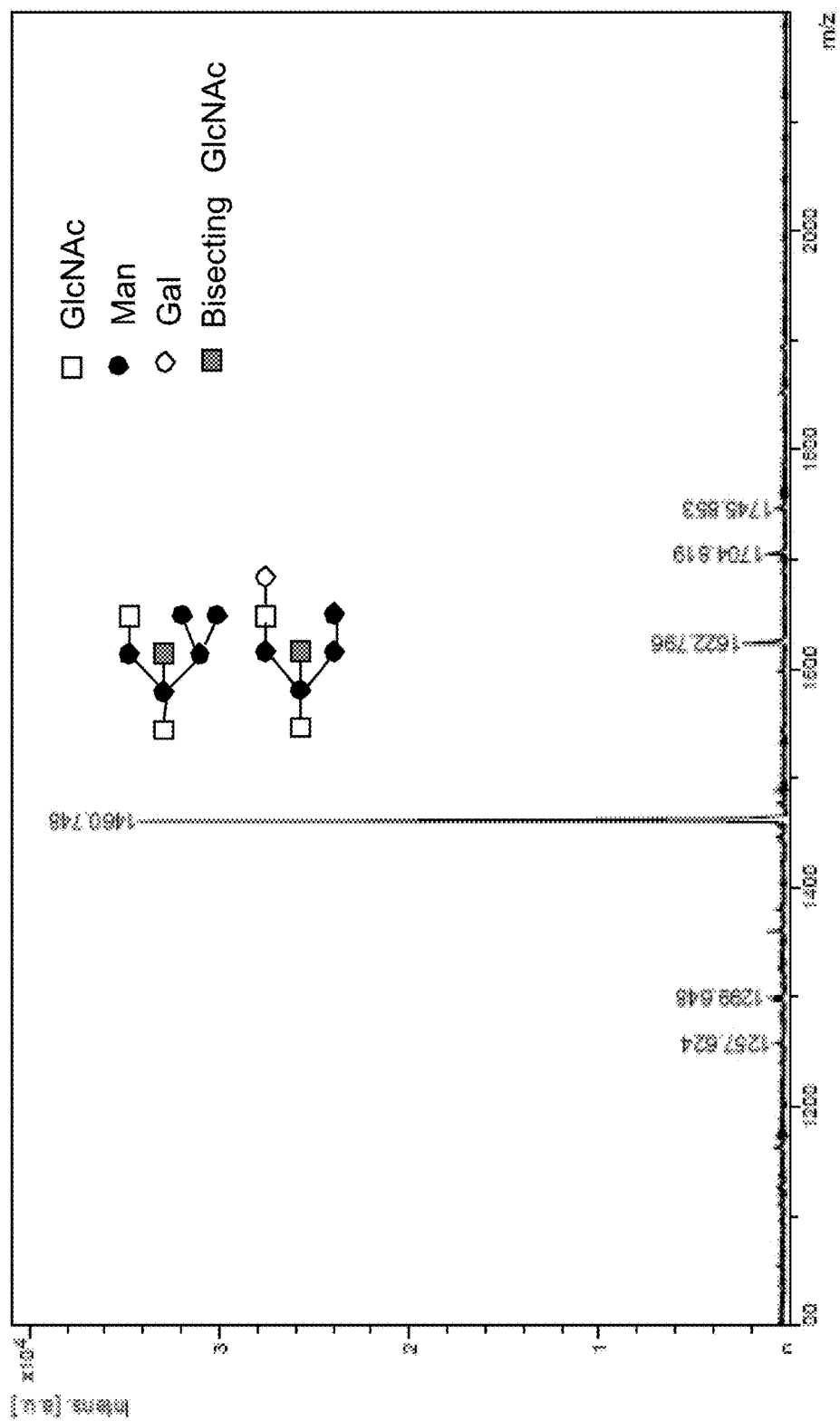

FIGS. 3A, 3B, and 3C. Positive-ion MALDI-TOF mass spectra of the N-linked oligosaccharides released from Fc fragment of antibody C by consecutive treatment with Endo S and PNGase F or with Endo S and Endo H. (FIG. 3A) Spectrum of glycans released by treatment with Endo S. (FIG. 3B) Spectrum of Endo S-resistant carbohydrates released by subsequent treatment with PNGase F, resulting in an isolated signal at m/z=1663 (possibly corresponding to hybrid- or complex-type structures as schematically depicted). (FIG. 3C) Spectrum of glycans released by subsequent treatment with the hybrid-type structure specific enzyme Endo H (hybrid-type structures corresponding to m/z=1460 released by Endo H treatment are schematically depicted).

Figure 4A:
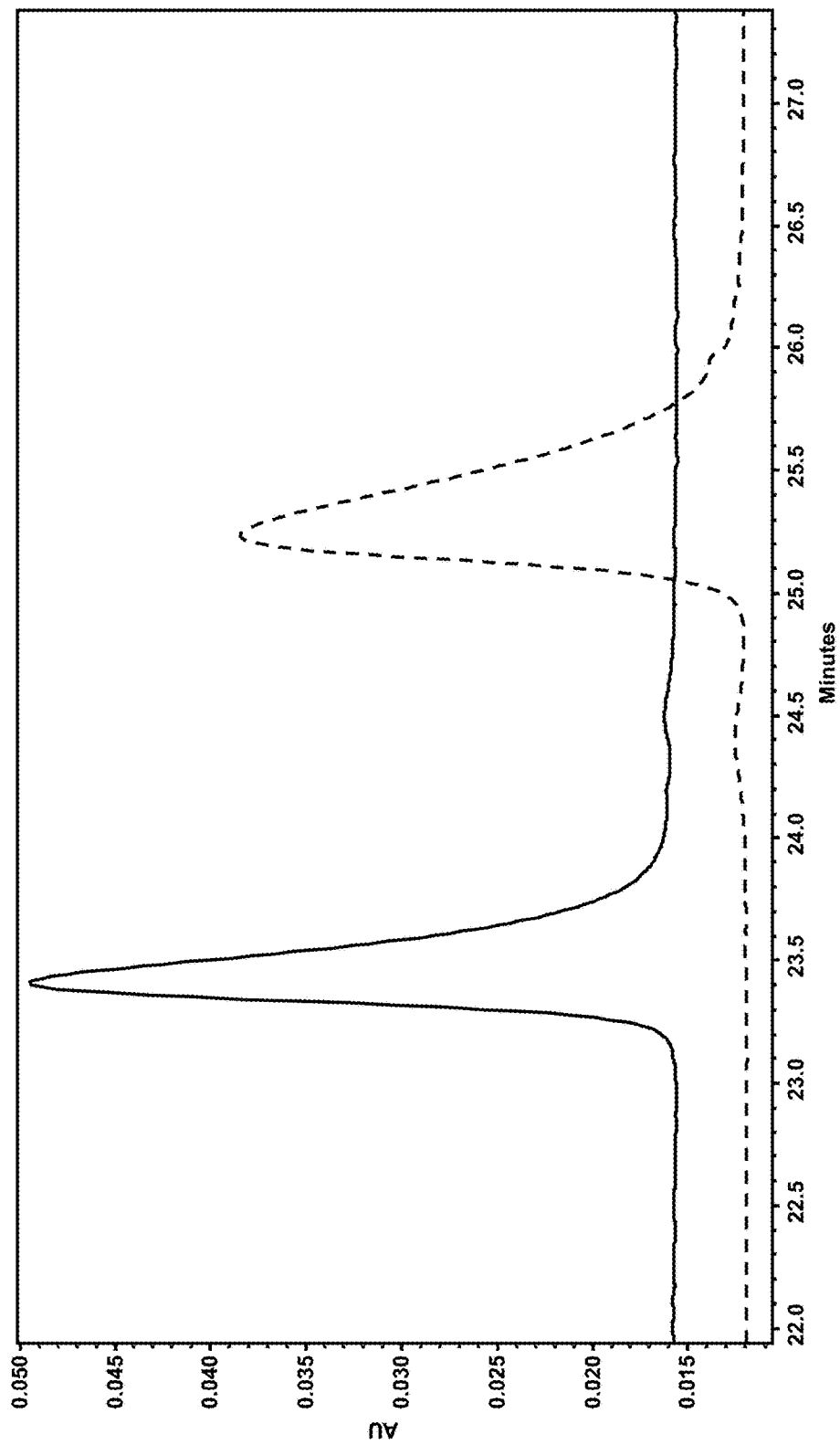
Figure 4B:
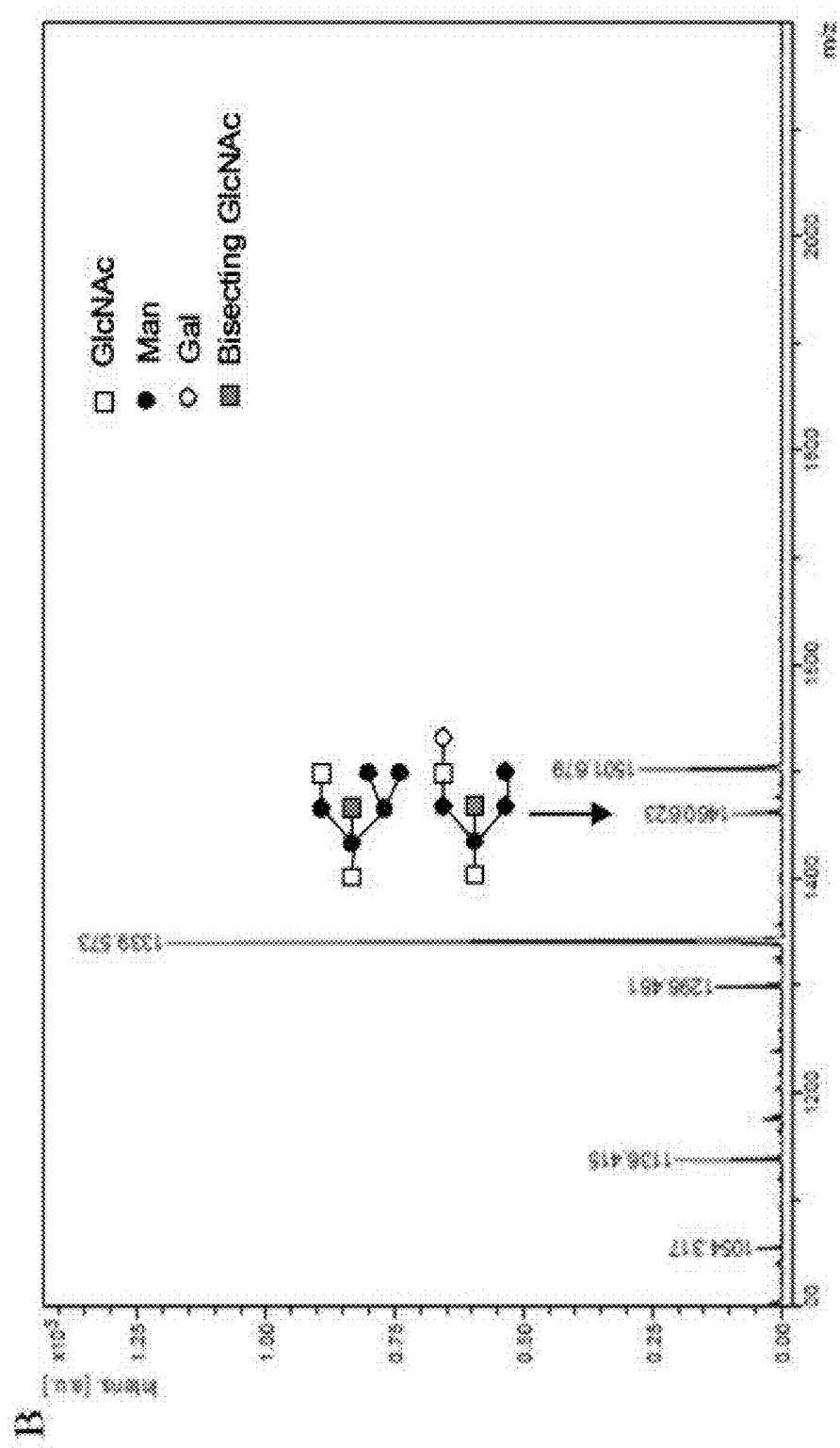

FIGS. 4A and 4B. Deglycosylation of the Fc fragment of antibody C monitored by CE-SDS MW analysis (FIG. 4A) and positive-ion MALDI-TOF mass spectrometry (FIG. 4B). (FIG. 4A) Overlay of electropherogram of the non-reduced Fc fragment without glycosidase treatment (dashed line) and treated with a combination of Endo S and Endo H (solid line). (FIG. 4B) Mass spectra of the N-linked oligosaccharides released from the Fc fragment treated with Endo S and Endo H. Hybrid-type structures corresponding to m/z=1460 released by Endo H are schematically depicted.

Figure 5A:
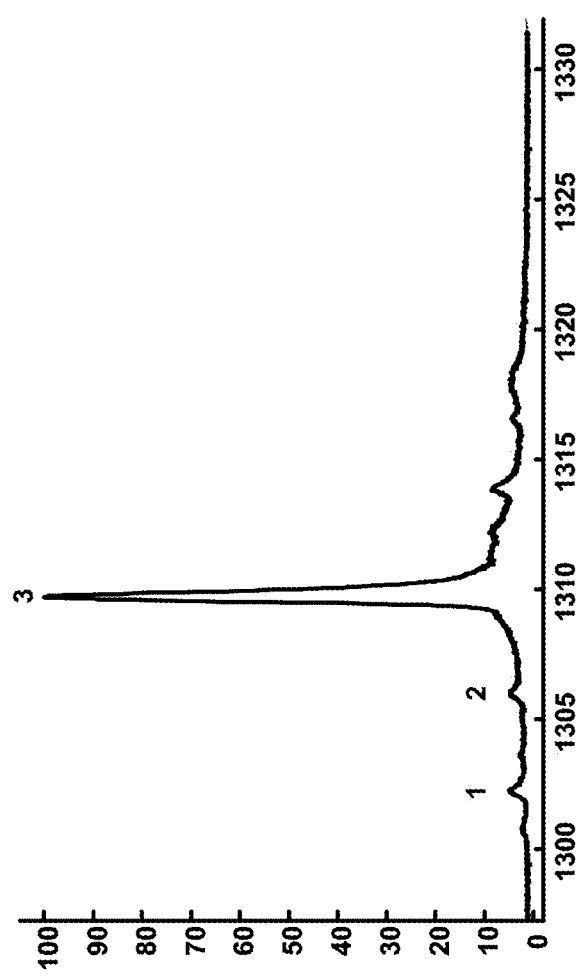
Figure 5B:
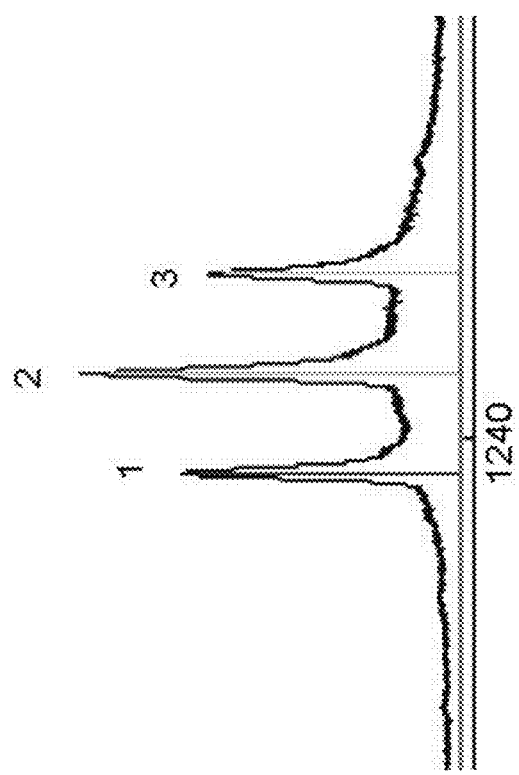
Figure 5C:
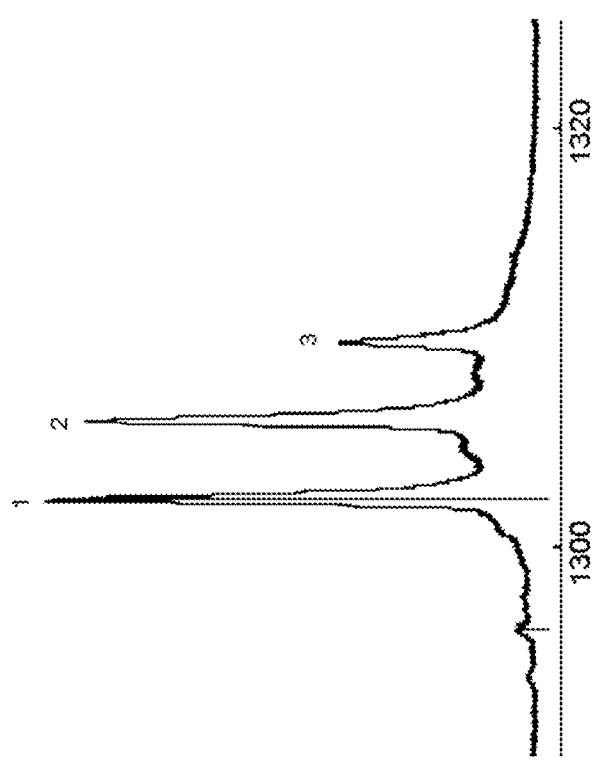

FIGS. 5A, 5B, and 5C. ESI-MS spectra of Fc fragments after treatment with Endo S and Endo H. (FIG. 5A) Fc fragments of antibody A, (FIG. 5B) Fc fragments of antibody B, (FIG. 5C) Fc fragments of antibody C. Peak 1: Fc-GlcNAc/GlcNAc, Peak 2: Fc-GlcNAc/GlcNAc+Fuc, Peak 3: Fc-GlcNAc+Fuc/GlcNAc+Fuc.

Figure 6A:
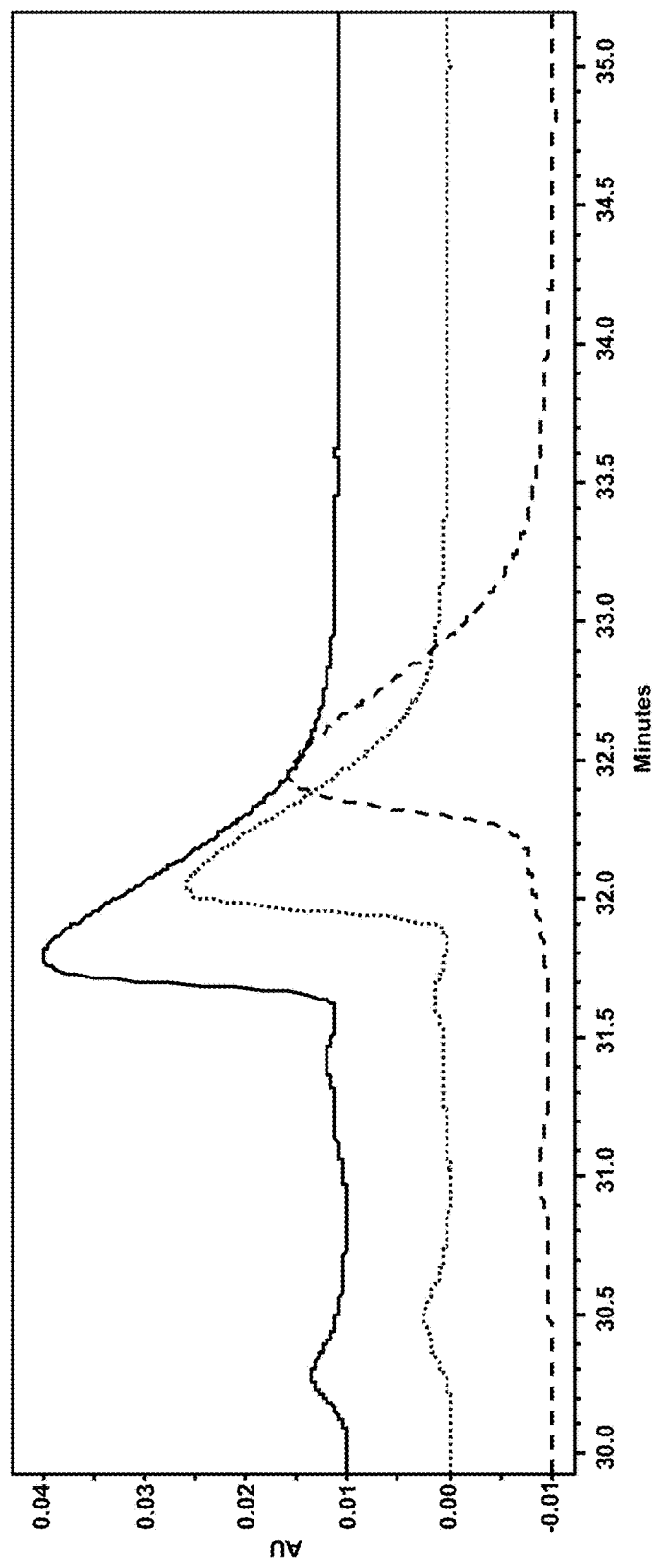
Figure 6B:
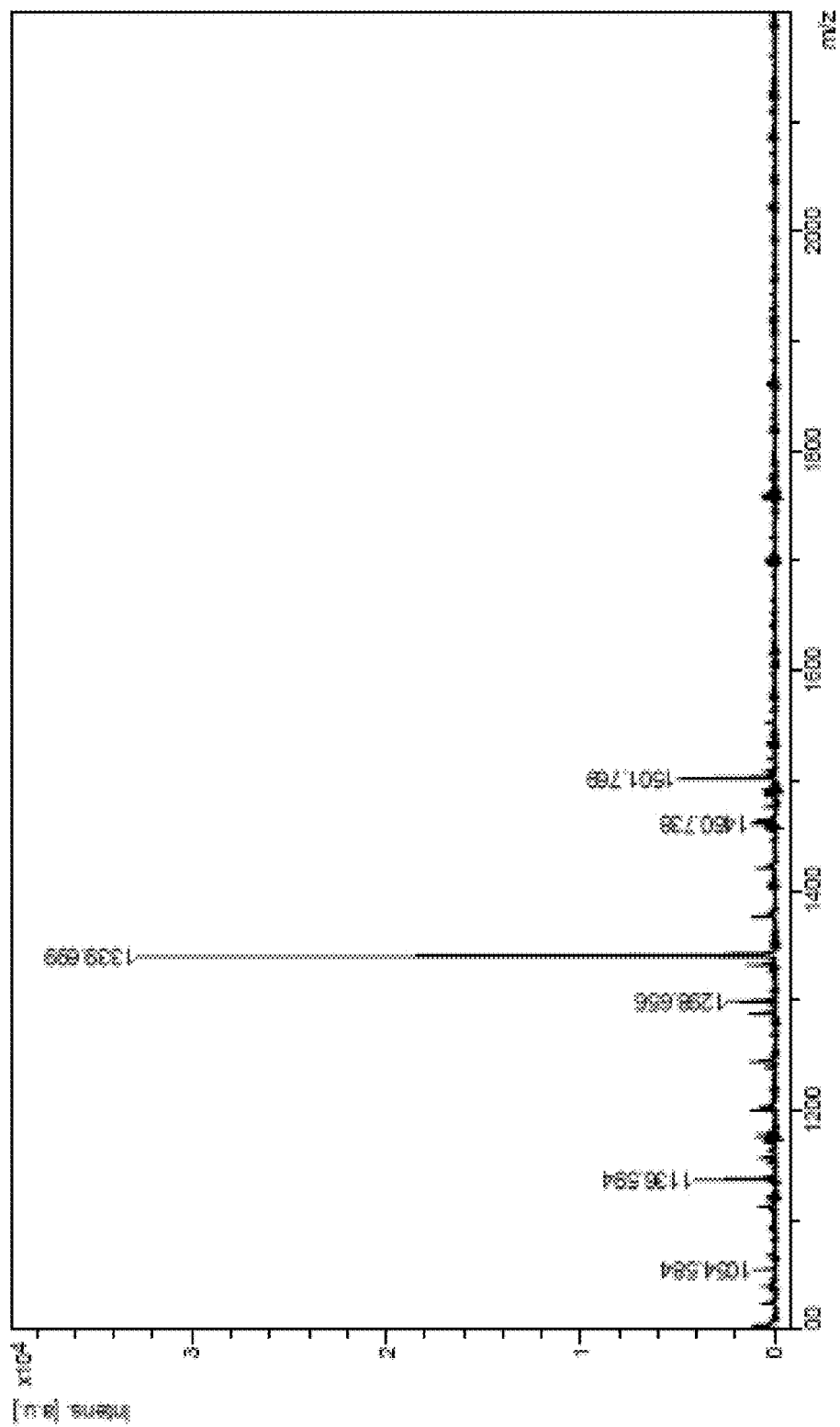

FIGS. 6A and 6B. Deglycosylation of antibody C monitored by CE-SDS (FIG. 6A) and positive-ion MALDI-TOF mass spectrometry (FIG. 6B). (FIG. 6A) Electropherograms of non-reduced IgG are shown before and after enzymatic treatment: Antibody C without enzymatic treatment (dashed line) and deglycosylated with PNGase F (dotted line) or combined treatment with Endo S and Endo H (solid line). (FIG. 6B) Mass spectra of the N-linked oligosaccharides released from entire IgG treated with Endo S and Endo H.

FIG. 7. N-linked oligosaccharide biosynthetic pathway leading to complex- or hybrid-type structures. M1: mannosidase I, β1,2-N-acetylglucosaminyltransferase I, G3: β1,4-N-acetylglucosaminyltransferase III, Gt: β1,4-galactosyltransferase.

Figure 8A:
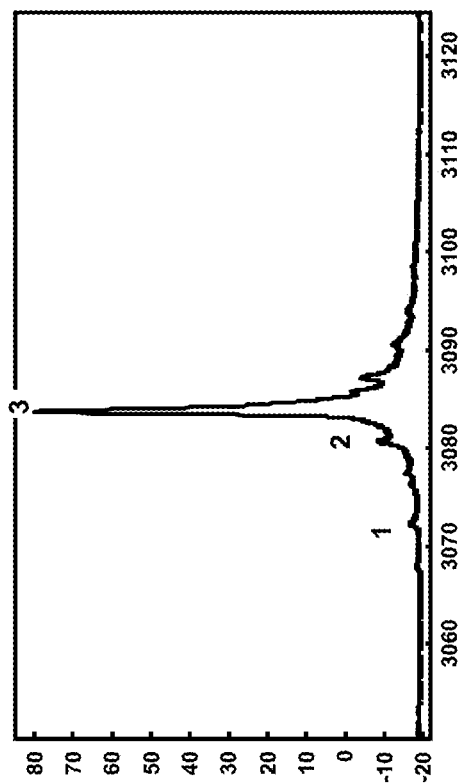
Figure 8B:
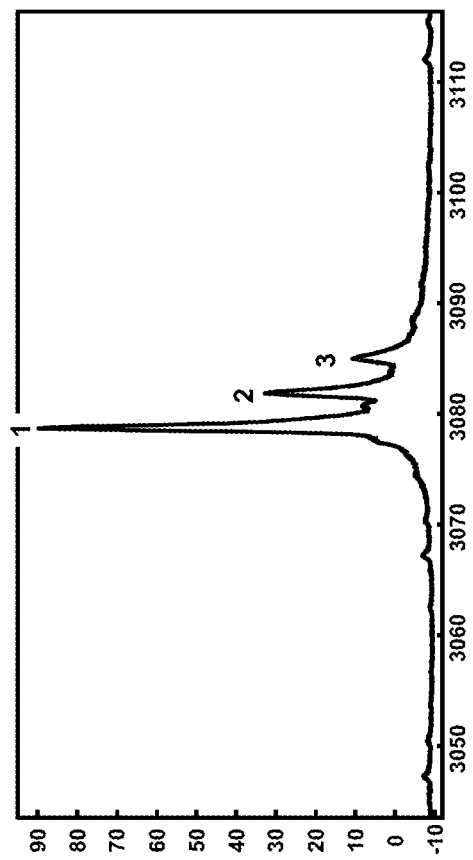

FIGS. 8A and 8B. ESI-MS spectra of entire IgGs after treatment with Endo S and Endo H. (FIG. 8A) antibody A, (FIG. 8B) antibody D. Peak 1: Fc-GlcNAc/GlcNAc, Peak 2: Fe-GlcNAc/GlcNAc+Fuc, Peak 3: Fc-GlcNAc+Fuc/GlcNAc+Fuc.

Figure 9A:
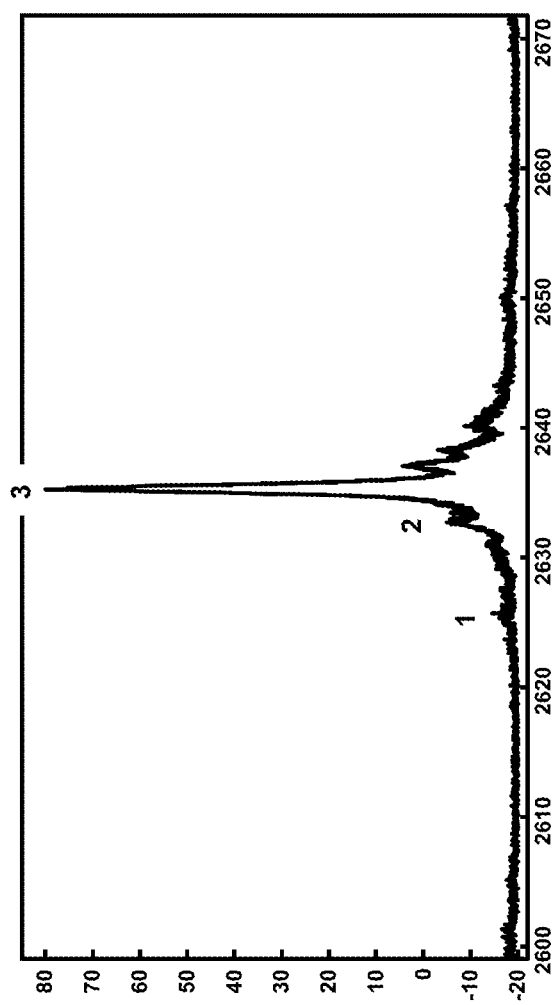
Figure 9B:
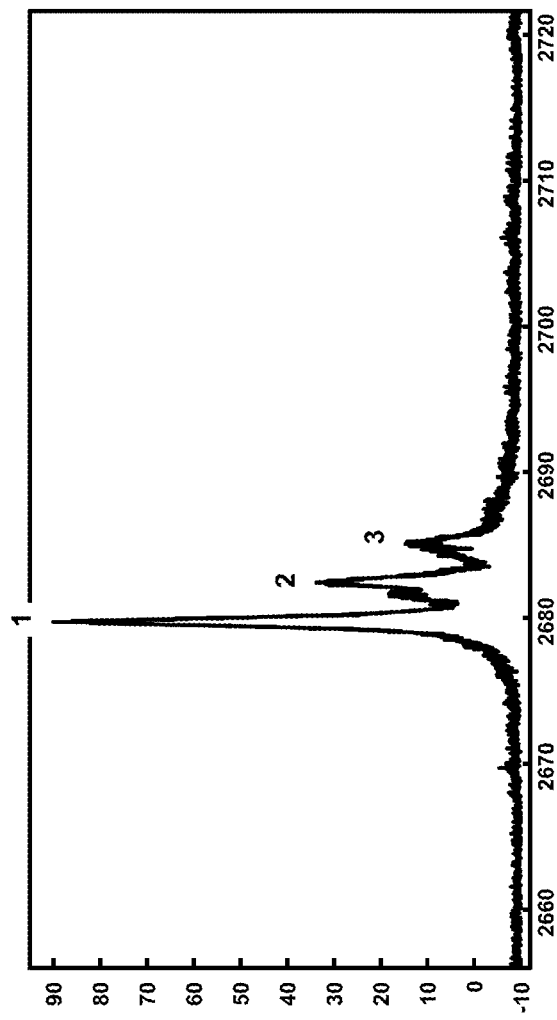

FIGS. 9A and 9B. LC-MS spectra of entire IgGs after treatment with Endo S and Endo H. (FIG. 9A) antibody A, (FIG. 9B) antibody D. Peak 1: Fc-GlcNAc/GlcNAc, Peak 2: Fe-GlcNAc/GlcNAc+Fuc, Peak 3: Fc-GlcNAc+Fuc/GlcNAc+Fuc.

EXAMPLES

Example 1: Methods

Generation of Fc from Human IgG

Four different human IgGs with a different content of a-fucosylated glycans, determined according to Papac et al., 1998 (content in brackets), were used for analysis of the a-fucosylation distribution: wildtype antibody A (2.12%), glycoengineered antibody B (47.0%), glycoengineered antibody C (69.6%), and glycoengineered antibody D (85%).

The proteins were incubated for 72 hours at 25° C. in 50 mM Tris pH 8.0, 150 mM NaCl with 0.42 U plasmin (Roche) per milligram. Cleaved Fc was separated from Fab-fragments using a Protein A affinity column (5 ml HiTrap™ Protein A HP column, GE Healthcare) equilibrated and washed (5 column volumes (CV)) with buffer A (50 mM Tris pH 8.0, 100 mM glycine, 150 mM NaCl). Fc was eluted by a pH-step using buffer B (50 mM Tris pH 3.0, 100 mM glycine, 150 mM NaCl). Fractions containing Fc were pooled and neutralized by adding 1:40 (v/v) 2 M Tris pH 8.0. Samples were concentrated to a volume of 2.5 ml using ultra concentrators (Vivaspin 15R 10'000 MWCO HY, Sartorius) and subsequently applied to a PD-10 desalting column (GE Healthcare) equilibrated with 2 mM MOPS pH 7.4, 150 mM NaCl, 0.02% (w/v) $NaN_3$. Purified protein was frozen in liquid nitrogen and stored at −80° C.

Release of N-Linked Oligosaccharides from Human Fc

Different enzymes were used for hydrolyzing the N-linked glycans of human IgG. The N-linked oligosaccharides were cleaved from 1 mg of Fc by incubation with 0.005 U recombinant PNGase F (QAbio, Vista Monte, USA). For release of carbohydrates from Fc using non-tagged Endo S (Genovis), samples were incubated with either a molar ratio of 1:20 of Endo S alone or in combination with 0.1 U/mg Endo H (QAbio). All reactions were incubated in 20 mM Tris pH 8.0 at 37° C. for 16 h.

For analyzing carbohydrates spared by Endo S, Fc was purified after Endo S treatment by affinity chromatography using Protein A and subsequently digested with either PNGase F or Endo H, as described above.

Release of N-Linked Oligosaccharides from Entire Human IgG

The N-linked glycans of human IgG were released using different enzymes. The N-linked oligosaccharides were cleaved from 1 mg of IgG by incubation with 0.005 U of recombinant PNGase F (QAbio) in 20 mM Tris pH 8.0 at 37° C. for 16 h. For release of carbohydrates from IgG using non-tagged Endo S (Genovis), samples were applied to a NAP-5 desalting column (GE Healthcare) equilibrated with 20 mM Tris pH 8.0. Eluted sample was concentrated to a final concentration of 4 mg/ml using ultra concentrators (Amicon 5'000 MWCO, Millipore) and incubated with a molar ratio of 1:7 of Endo S combined with 0.1 U/mg Endo H (QAbio) at 37° C. for 16 h.

Carboxypeptidase B Treatment

To remove heterogenicity caused by C-terminal lysine residues, after deglycosylation samples were further incubated with carboxypeptidase B (Roche; 1 mg/ml). Therefore 1 μl carboxypeptidase B per 50 μs human Fc or entire antibody was added to the Endoglycosidase reaction and incubated again for 1 h at 37° C.

MALDI-TOF Mass Spectrometry Analysis of Released Oligosaccharides

Neutral oligosaccharide profiles of the human Fc or entire antibody were analyzed by mass spectrometry (Autoflex, Bruker Daltonics GmbH) in positive ion mode (Papac et al., 1998).

Purification of Deglycosylated Human Fc or Entire Antibody

Fc or entire IgG was separated from enzymes and cleaved carbohydrates by Protein A affinity chromatography using Agilent HPLC 1100 series (Agilent Technologies). Samples were applied to Protein A matrix (Poros 20 A; Applied Biosystems) packed in a guard column 2×20 mm C-130B (Upchurch Scientific) equilibrated with buffer A (50 mM Tris, 100 mM glycine, 150 M NaCl, pH 8.0). After washing with 5.5 CV of buffer A, human Fc or entire IgG was eluted by a pH-step using buffer B (50 mM Tris, 100 mM glycine, 150 M NaCl, pH 3.0) over 8.3 CV. The fraction containing the protein was neutralized by adding 1:40 (v/v) 2 M Tris pH 8.0.

The purified protein was subsequently further used for either treatment with enzymes to analyze non-cleaved carbohydrates, CE-SDS analysis or ESI-MS.

CE-SDS MW Analysis

Deglycosylation was monitored by CE-SDS-MW analysis, using Beckman PA800 with UV detection. The buffer of 100 μg of each Protein A purified sample was exchanged to 20 mM Tris pH 8.0 using spin concentrators (5000 MWCO, Millipore). Non-reduced samples were prepared as described in SDS-MW Analyses Guide using the ProteomeLab SDS-MW Analysis Kit (Beckman Coulter). The final protein concentration was 1 mg/ml. Samples were applied to a preconditioned bare fused silica capillary (50 μm ID×30.2 cm). Pre-conditioning and separation were performed according to the instruction manual.

Sample Preparation for ESI-MS

The buffer of Protein A purified samples was exchanged to 2 mM MOPS pH 7.4, 150 mM NaCl, 0.02% (w/v) $NaN_3$ using spin concentrators (5000 MWCO, Millipore). Proteins were frozen in liquid nitrogen and stored at −80° C.

ESI-MS Analysis of Glycan Structures of Human Fc and Entire IgG by Direct Infusion (Off Line Detection)

Desalting by Size Exclusion Chromatography:

20-50 μg (up to 90 μl) of Fc after treatment of antibody with the proteases plasmin and carboxypeptidase B and with endo-glycosidases Endo S and Endo H, or entire IgG after treatment with Endo S, Endo H and carboxypeptidase B, were injected onto a Sephadex G25 self-packed ECO SR column (5×250 mm; KronLab) equilibrated with 2% formic acid, 40% acetonitrile at a flow rate of 0.5 ml/min for 30 minutes. The injected protein sample was desalted applying an 8 minute isocratic elution with 2% formic acid, 40% acetonitrile at a flow rate of 1 ml/min. The elution of the desalted protein was recorded by UV at 280 nm and the eluting sample (volume about 200-300 μl) was collected in a 1.5 ml reaction vial. An aliquot of the desalted sample was manually filled into a metal coated glass needle (Proxeon Biosystems Nano ESI-needles, cat# ES387), inserted into the nanospray source of the mass instrument and sprayed into a ESI-Q-TOF II mass spectrometer from Waters or into a Q-Star Elite mass spectrometer from Applied Biosystems.

MS Parameters for Direct Infusion:

A) Of Plasmin-Treated Samples (Human Fc) on a Q-TOF II Instrument (Waters)

MS spectra were acquired using a capillary voltage of 1000 V, a cone voltage of 30 V in a mass range from 1000-2000 m/z in positive ion mode using a source temperature of 80° C. Desolvation temperature was off. MS data were acquired for approx 2-3 minutes by the respective instrument software.

B) Of Entire Antibody on a MaXis-ESI-MS Instrument (Bruker)

MS spectra were acquired using a NanoMate device as spray interface. The values for data acquisition at the MS instrument were set to 400 Vpp (funnel RF), 120 eV (ISCID energy) and 400 Vpp (Multipol RF) regarding the transfer parameters, 5.0 eV (ion energy) and 300 m/z (low mass) for the quadrupole parameters, 15 eV (collision energy) and 3000 Vpp (collision RF) adjusting the collision cell and 800

Vpp, 160 μs for transfer time and 20 μs prepulse storage at the ion cooler. Data were recorded at a mass range from 1000-4000 m/z in positive ion mode.

Molar masses of dimeric Fc-fragments and entire antibody, containing different combinations of glycan structures truncated by the endoglycosidases applied, i.e GlcNAc/GlcNAc, GlcNAc+Fuc/GlcNAc and GlcNAc+Fuc/GlcNAc+Fuc, were determined from the respective m/z pattern of the Fc fragment or entire antibody species using an in-house developed software. The relative ratios of the various residually glycosylated dimeric Fc fragments or entire antibodies were calculated with the same in-house software using the sum of peak areas of the m/z spectrum of a distinct glycosylation variant of the dimeric Fc-fragment or entire antibody.

ESI-MS Analysis of Glycan Structures of Entire IgG by LC-MS (on Line Detection)

LC-MS was performed on a Dionex HPLC system (Dionex Ultimate 3000) coupled to a Q-TOF II mass spectrometer (Waters). The chromatographic separation was performed on a ACE C4 column (5 μm particle size, 300 A pore size, 1×30 mm; Advanced Chromatography Technologies). Eluent A was 0.1% formic acid, eluent B was 99.9% acetonitrile and 0.1% formic acid. The flow rate was 100 μl/min, the separation was performed at 75° C. and 2 (10 μl) of an intact antibody sample treated with Endo S and Endo H, but without plasmin treatment, were used.

TABLE 1

Parameters for LC-MS.

| Time (min.) | % B | remark |
|---|---|---|
| 0 | 25 | waste |
| 3 | 25 | |
| 3.1 | 25 | |
| 3.5 | 25 | switch to MS |
| 4.0 | 25 | |
| 9.0 | 50 | |
| 9.5 | 100 | |
| 12.5 | 100 | |
| 12.6 | 25 | |
| 14.9 | 25 | switch to waste |
| 15.0 | 255 | stop MS-detection |

MS spectra were acquired using a capillary voltage of 2700 V, a cone voltage of 80 V in a mass range from 1000-4000 m/z in positive ion mode using a source temperature of 100° C. Desolvation temperature was set to 200° C. MS data were acquired for approximately 11.4 minutes (gradient time 3.5 to 14.9 min) by the respective instrument software.

Molar masses of intact antibody (consisting of two heavy chains and two light chains) containing different combinations of glycan structures truncated by the endoglycosidases applied, i.e GlcNAc/GlcNAc, GlcNAc+Fuc/GlcNAc and GlcNAc+Fuc/GlcNAc+Fuc, were determined from the respective m/z pattern of the antibody species using an in-house developed software. The relative ratios of the various residually glycosylated intact antibodies were calculated with the same in-house software using the sum of peak areas of the m/z spectrum of a distinct glycosylation variant of the intact antibody.

The ratio of non-fucosylated heavy chains was determined by reducing the EndoS and EndoH-treated antibody with TCEP (Tris(2-carboxyethyl)phosphine hydrochloride) and performing an LC-MS analysis as described before, using the same column type and gradient setting but some modified parameters for MS data acquisition. MS parameters were the same as described before, but cone voltage was set to 25 V and mass range was from 600-2000 m/z.

Example 2: Results

Deglycosylation of Fc

N-Glycosidase F, also known as PNGase F, is a highly specific deglycosidase that cleaves between the innermost N-acetylglucosamine of high mannose-, hybrid-, and complex-type N-linked oligosaccharides and the asparagine residue of the glycoprotein to which the glycan is attached (Tarentino et al., 1985). Treatment of the Fc fragments of antibody A and C with PNGase F according to the instructions of the manufacturer was monitored by CE-SDS. Under these conditions PNGase F quantitatively removes the glycan moiety of both analyzed samples, resulting in a mobility shift of the main peak from $3.79\times10^{-5}$ to $3.9\times10^{-5}$ (FIG. 2). Endo S cleaves the chitobiose core of N-linked oligosaccharides, leaving the first N-acetylglucosamine residue—and an α-fucose residue in case of fucosylated carbohydrates—attached to the protein. The CE-analysis of a such digested glycoengineered sample revealed that approximately 10% of the protein were still undigested (FIG. 2a, Table 2), as demonstrated by a peak with a mobility of $3.84\times10^{-5}$. Subsequent analysis by PNGase F treatment indicated that the Endo S resistant carbohydrates were entirely of hybrid structure suggesting specificity of this enzyme for complex carbohydrates. This result could be corroborated by the quantitative Endo S digestion of wild-type antibody A which resulted in homogenously deglycosylated protein (FIG. 2b).

TABLE 2

Peak area of enzyme-treated Fc fragments evaluated by CE-SDS.

| | Peak area [%] | |
|---|---|---|
| Antibody, enzyme | Non-cleaved | Cleaved |
| A, no enzyme | 99.3 | 0.7 |
| A, PNGase F | 1.3 | 98.7 |
| A, Endo S | 1.8 | 98.2 |
| C, no enzyme | 100.0 | 0.0 |
| C, PNGase F | 0.3 | 99.7 |
| C, Endo S | 10.6 | 89.4 |

To confirm this hypothesis, Endo S-treated Fc of antibody C was purified by affinity chromatography to remove the enzyme and cleaved carbohydrates, and subsequently incubated with PNGase F to remove the entire glycan moiety. The hydrolyzed carbohydrates were further analyzed by MALDI TOF MS. The obtained spectra showed that Endo S is discriminating (i.e. sparing) either complex- or hybrid-type bisected structures that are corresponding to m/z=1663 (FIG. 3b).

Further experiments were performed to determine whether the discriminated carbohydrates are complex- or hybrid-type bisected structures. After purification by affinity chromatography, the Endo S-treated Fc fragment of antibody C was incubated with PNGase F or Endoglycosidase H (Endo H). Endo H is a recombinant glycosidase that cleaves within the chitobiose core of high mannose- and hybrid-type N-linked oligosaccharides of glycoproteins. It is not able to cleave within complex structures. MALDI TOF MS spectra showed that the carbohydrates discriminated by Endo S are cleaved by Endo H, resulting in a main peak of m/z=1460 (FIG. 3c). These data clearly show that Endo S is not able to release hybrid-type bisected carbohydrates from the asparagine-linked N-acetylglucosamine.

To obtain homogenously deglycosylated material that only varies in its α-linked fucose content, a combined treatment of the Fc fragment of antibody C with Endo S and Endo H was performed resulting in a protein that was quantitatively deglycosylated after the first GlcNAc residue as observed by CE-SDS (FIG. 4a). MALDI-TOF MS analysis showed that the hybrid bisected structures (m/z=1460) are released by combination of these two enzymes (FIG. 4b). To confirm that there is no other carbohydrate attached to the N-acetylglucosamine with or without an α-linked fucose residue, Endo S- and Endo H-treated Fc fragment of antibody C was incubated with PNGase F. No MALDI TOF spectra could be obtained after this treatment suggesting that no other carbohydrates were remaining that cannot be cleaved by Endo S or Endo H (data not shown).

Determination of the Fucose Distribution in a Fc Preparation

To quantify the distribution of the fucose linked to the N-acetylglucosamine residue attached to the Fc, ESI-MS analyses were performed. After incubation with Endo S and Endo H before separation by affinity chromatography, the Fc domains of antibodies A, B and C (generated by plasmin digestion) were treated with carboxypeptidase B to remove heterogeneity introduced by C-terminal lysine.

ESI-MS spectra revealed Fc fragments with either two, one or no fucose linked to the residual GlcNAc still attached to the protein after EndoS/EndoH treatment (FIG. 5). Distribution of these three fucose species is summarized for the investigated three different IgGs A, B and C (calculated as relative ratio of the sum of peak areas in the m/z-spectra). The results correlate well with the fucose content determined by MALDI-TOF MS (Table 3).

TABLE 3

Comparison of the a-fucosylation degree determined by mass spectrometry for Fc fragment of antibody A, B and C.

| | | ESI-MS | | |
|---|---|---|---|---|
| | MALDI-TOF Non-fuc [%] | 2 fucose [%] | 1 fucose [%] | 0 fucose [%] | Non-fuc [%] |
| A | 2.12 | 94 | 3 | 3 | 4.5 |
| B | 47.0 | 29 | 41 | 30 | 50.5 |
| C | 69.6 | 20 | 40 | 40 | 60.0 |

Deglycosylation of Entire IgG

For deglycosylation of an entire IgG by combined treatment with Endo S and Endo H, cleavage conditions had to be optimized. Deglycosylation with a molar ratio of Endo S to IgG of 1:20, as was used for deglycosylation of the Fc fragment, was insufficient to deglycosylate entire IgG. Increasing the concentration of Endo S to a molar ratio of 1:7 was sufficient to get homogenously deglycosylated material that only varies in its α-linked fucose content observed by CE-SDS (FIG. 6a). MALDI-TOF analysis showed that the carbohydrates are released by combined treatment with Endo S and Endo H (FIG. 6b). Using this approach it is possible to analyze the allocation of fucose per IgG without separate generation of the Fc-fragment.

Determination of the Fucose Distribution of Entire IgG

Quantification of the distribution of fucose linked to the innermost N-acetylglucosamine residue of N-linked glycans of entire IgGs was performed using wildtype antibody A (2.12% a-fucosylation) and glycoengineered antibody D (85.0% a-fucosylation). After combined treatment with Endo S and Endo H, both IgGs were incubated with carboxypeptidase B to remove heterogeneity introduced by C-terminal lysine. The antibodies were subsequently purified by affinity chromatography.

Allocation of the core fucose per IgG was determined using two different methods. The pattern of the m/z-spectra obtained by ESI-MS off line detection revealed IgG-species with either two, one or no fucose attached to the residual GlcNAc after EndoS/EndoH treatment (FIG. 8). Distribution of these three fucose species is summarized for the investigated two different IgGs A and D (calculated as relative ratio of the sum of peak areas in the m/z-spectra) (Table 4).

LC-MS analyses were also performed to determine the allocation of fucose per IgG (FIG. 9). For both IgGs, m/z-spectra showed a similar ratio of species with either two, one or no fucose attached as observed in ESI-MS offline detection, (Table 4). Peak areas below 5% are in the detection sensitivity of the methods for entire IgG. Ratio for non-fucosylated heavy chain is presented in Table 4, column Non-fuc [%].

TABLE 4

Comparison of the a-fucosylation degree and fucose allocation determined by ESI-MS and LC-MS analyses for antibody A and D.

| | ESI-MS | | | | LC-MS | | | |
|---|---|---|---|---|---|---|---|---|
| | 2 fucose [%] | 1 fucose [%] | 0 fucose [%] | Non-fuc [%] | 2 fucose [%] | 1 fucose [%] | 0 fucose [%] | Non-fuc [%] |
| A | 92 | 5 | <5 | 8 | 94 | 6 | <5 | 12 |
| D | 9 | 24 | 67 | 81 | 10 | 24 | 66 | 80 |

What is claimed is:

1. A method for detecting the presence or absence of fucose residues within a homogenously deglycosylated immunoglobulin G antibody, said method comprising:
   (a) providing an antibody preparation comprising a glycosylated immunoglobulin G antibody,
   (b) removing heterogeneous saccharide residues from the glycosylated immunoglobulin G antibody with the enzyme endoglycosidase S and the enzyme endoglycosidase H, thereby obtaining said homogenously deglycosylated immunoglobulin G antibody,
   (c) removing other heterogenous residues from said homogenously deglycosylated immunoglobulin G antibody with an enzyme, and
   (d) analyzing said homogenously deglycosylated immunoglobulin G antibody for the presence or absence of fucose residues, wherein the linkage information on the presence or absence of fucose residues within the homogenously deglycosylated immunoglobulin G antibody is maintained.

2. The method of claim 1, wherein said method further comprises purifying said homogenously deglycosylated immunoglobulin G antibody prior to analyzing said homogenously deglycosylated immunoglobulin G antibody for the presence or absence of fucose residues.

3. The method of claim 1, wherein said method further comprises determining the quantity of fucose residues among said homogenously deglycosylated immunoglobulin G antibody.

4. The method of claim 1 or claim 3, wherein said method further comprises determining the distribution pattern of fucose residues among said homogenously deglycosylated immunoglobulin G antibody.

5. The method of claim 1 or claim 3, wherein said method further comprises determining the distribution pattern of fucose residues per homogenously deglycosylated immunoglobulin G antibody.

6. The method of claim 1, wherein removing other heterogeneous residues from the homogenously deglycosylated immunoglobulin G antibody in step (c) is performed by one or more enzymes selected from the group consisting of plasmin and carboxypeptidase B.

7. The method of claim 1, wherein analyzing the homogenously deglycosylated immunoglobulin G antibody for the presence or absence of fucose residues in step (d) is performed by an analysis selected from the group consisting of liquid-chromatography-mass spectrometry analysis, capillary electrophoresis-sodium dodecyl sulfate molecular weight analysis, and electrospray ionization mass spectrometry analysis.

8. A method for detecting the presence or absence of fucose residues within a homogenously deglycosylated immunoglobulin G antibody, said method comprising:
(a) providing an antibody preparation comprising a glycosylated immunoglobulin G antibody,
(b) removing heterogeneous saccharide residues from the glycosylated immunoglobulin G antibody with the enzyme endoglycosidase S and the enzyme endoglycosidase H, thereby obtaining said homogenously deglycosylated immunoglobulin G antibody,
(c) removing C-terminal lysine residues from said homogenously deglycosylated immunoglobulin G antibody with carboxypeptidase B, and
(d) analyzing said homogenously deglycosylated immunoglobulin G antibody for the presence or absence of fucose residues by liquid-chromatography-mass spectrometry analysis, capillary electrophoresis-sodium dodecyl sulfate molecular weight analysis, and electrospray ionization mass spectrometry analysis, wherein the linkage information on the presence or absence of fucose residues within the homogenously deglycosylated immunoglobulin G antibody is maintained.

9. The method of claim 8, wherein said method further comprises purifying said homogenously deglycosylated immunoglobulin G antibody prior to analyzing said homogenously deglycosylated immunoglobulin G antibody for the presence or absence of fucose residues.

10. The method of claim 8 or claim 9, wherein said method further comprises determining cooperative fucosylation in said antibody preparation during fermentation.

* * * * *